United States Patent
Poulet

(10) Patent No.: US 6,551,598 B2
(45) Date of Patent: Apr. 22, 2003

(54) VACCINATION AGAINST CANINE HERPESVIROSIS AND VACCINES THEREFOR

(75) Inventor: Hervé Poulet, Sainte Foy les Lyon (FR)

(73) Assignee: Merial, Lyons (FR)

(*) Notice: Subject to any disclaimer, the term of this patent is extended or adjusted under 35 U.S.C. 154(b) by 0 days.

(21) Appl. No.: 09/766,083

(22) Filed: Jan. 18, 2001

(65) Prior Publication Data

US 2001/0028884 A1 Oct. 11, 2001

Related U.S. Application Data

(60) Provisional application No. 60/193,227, filed on Mar. 30, 2000.

(30) Foreign Application Priority Data

Jan. 21, 2000 (FR) .......................... 2000 00797

(51) Int. Cl.⁷ ................. A61K 39/245; A61K 39/12; A61K 51/00; A61K 212/00
(52) U.S. Cl. ................. 424/229.1; 424/9.1; 424/93.1; 424/818; 424/78.31; 424/450; 530/228; 530/230; 530/811; 530/812; 530/815; 530/816; 530/826; 514/44; 435/2
(58) Field of Search ............... 424/229.1, 818, 424/78.31, 450, 93.1, 9.1; 531/228, 230; 530/815, 816, 812, 811, 826; 435/2; 514/44

(56) References Cited

U.S. PATENT DOCUMENTS

| | | | |
|---|---|---|---|
| 4,213,965 A | 7/1980 | Carmichael | |
| 5,753,235 A | * 5/1998 | Hannes et al. | 424/229.14 |
| 5,804,197 A | 9/1998 | Haanes et al. | |

FOREIGN PATENT DOCUMENTS

| | | |
|---|---|---|
| WO | WO 99/44633 | 9/1999 |
| WO | WO 99/51269 | 10/1999 |

OTHER PUBLICATIONS

Cox et al. (a) Vaccine, 1997, vol. 15, ppl. 248–256.*
Cox et al. (b) BioDrugs, 1999, vol. 12, pp. 439–453.*
Yamamoto etal. Immunobioliology of Bacterial CgG–DNA, pp. 26–27.*

Cruse et al. Illustrated Dictionary of Immunology, pp.309.*

Poulet et al. (1993) "L'herpesvirose Canine" Point Vét., vol. 25, pp. 69–75.

Pierson et al. (1998) "L'herpésvirose En Élevage Canin: Aspects Cliniques Et Diagnostic" recueil de Médecine Vétérinaire. vol. 174, No. 3–4, pp. 87–94.

Delisle F (1982) "L'herpesvirose Canine" Rec. Med. Vet. vol. 158, pp. 669–676.

Appel M (1987) "Canine Herpesvirus" Virus Infections of Vertebrates. vol. 1, Elsevier Science Publisher pp. 5–15.

Carmichael et al (1978) Small–plaque variant of canine herpesvirus with reduced pathogenicity for newborn pups. Infect Immun. vol. 20, No. 1, pp. 108–114.

Limcumpao et al (1991) "Homologous and heterologous antibody responses of mice immunized with purified feline herpesvirus type 1 and canine herpesvirus glycoproteins" J Vet Med Sci. vol. 53, No. 3, pp. 423–432.

Engels et al.; "Die Seroepizootologie Der Caninen Herpesvirusinfektion In Der Schweiz Und Praliminare Versuche Mit Einer Vakzine", vol. 27, No. 4, 1980—pp. 257–267.

Pierson et al.; "L'Herpesvirose En Elevage Canin: Aspects Cliniques Et Diagnostic"; vol. 174, No. 3–4, Mar. 1998—pp. 87–94.

* cited by examiner

Primary Examiner—James Housel
Assistant Examiner—Bao Qun Li
(74) Attorney, Agent, or Firm—Frommer Lawrence & Haug, LLP; William S. Frommer; Thomas J. Kowalski

(57) ABSTRACT

Use of a CHV antigen for the preparation of a vaccine against canine herpesvirosis, which is intended to be administered to gestating bitches as close as possible to whelping, preferably during the final third of gestation, and which produces a high level of anti-CHV antibodies in gestating bitches at the time of whelping, inducing protection in the puppies by transfer of antibodies during suckling. Inactivated anti-CHV vaccine or subunit vaccines, which can be used for vaccinating gestating bitches to protect the puppies by transfer of antibodies.

59 Claims, No Drawings

VACCINATION AGAINST CANINE HERPESVIROSIS AND VACCINES THEREFOR

This application claims the benefit of U.S. Provisional Application No. 60/193,227 filed Mar. 30, 2000, and French Application No. 0000797 filed Jan. 21, 2000, and incorporates by reference said applications and such other applications or publications referred to in said provisional application.

The present invention relates to immunization or vaccination against canine herpesvirus. The invention relates in particular to an immunization or vaccination method, to suitable immunogenic compositions and vaccines and to the use thereof in the context of these methods.

Canine herpesvirus (or CHV) was described for the first time in 1965 (L. E. Carmichael, Am. J. Vet. Res., 1965, 26, 803–814). Infection with canine herpesvirus was then identified in many countries (USA, France, United Kingdom, Switzerland, Italy, Japan, Australia, New Zealand etc.). CHV is responsible for reproductive problems in canine breeding and most particularly for mortality in newborn puppies, which may give rise to significant losses in certain breeding kennels. It is also responsible for abortions and still-births. Infection with CHV is moreover suspected of reducing fertility in bitches. The transmission of CHV takes place via the venereal route, the oronasal route or the transplacental route.

CHV belongs to the family of Herpesviridae and to the subfamily of Alphaherpesvirinae. To date, only one type of CHV has been identified. This is an enveloped virus containing a double-stranded DNA molecule. The envelope contains several glycoproteins of viral origin. The glycoproteins gB, gC and gD are responsible for the induction of neutralizing antibodies in mice.

CHV is antigenically similar to feline herpesvirus (J. A. Limcumpao et al., Arch. Virol., 1990, 111, 165–176) but has no significant cross-neutralization (X. Xuan et al., Arch. Virol., 1992, 122, 359–365).

CHV is strongly dependent on its host and multiplies only on cells of canine origin (Pierson et al., recueil de Médecine Vétérinaire, March/April 1998, 174 No. 3/4, 87–94).

Newborn puppies are highly sensitive to infection with CHV during the first 3 weeks of life. The contamination occurs during whelping or the first few days of life. Consequently, it is not possible to vaccinate the puppies. The only means of protection available are hygiene measures such as heating the puppies with an infrared lamp and serotherapy. However, CHV is relatively non-immunogenic and it is difficult to prepare a good serum (L. B. Carmichael, J. Am. Vet. Med. Assoc., 1970, 156, 1714–1721).

Under natural conditions, puppies can be protected with the CHV-neutralizing antibodies present in the colostrum of seropositive bitches: in the absence of these antibodies, the puppies are highly sensitive to infection with CHV (D. L. Huxsoll and I. E. Hemelt, J. Am. Vet. Med. Assoc., 1970, 156, 1706–1713). The at-risk animals are puppies born from uninfected bitches in contact with excreting animals, and puppies born from latent but seronegative or weakly seropositive infected bitches. The CHV-neutralizing antibodies do not persist for a long time, and an animal can be infected and seronegative.

In puppies less than 3 weeks old, CHV causes a neonatal hepesvirosis which is often fatal. The incubation is rapid and the puppies die within a few days, usually with no symptoms other than sudden hypothermia and devastating nervous disorders, in the vast majority of cases before the 5-day-old stage. In the less acute forms, the hypothermia is followed by symptoms such as anorexia, depression, bradycardia, hypoglycemia, subcutaneous edema, erythema and ventral papules, soft yellowish-gray stools, abdominal pains, vomiting, incessant whining, pedaling and death within 24 to 72 hours in opisthotonus. The necropsic examination may reveal an enlarged spleen, serous effusion in the pleural and peritoneal cavities and visceral petechia (Pierson et al., recueil de Médecine Vétérinaire, March/April 1998, 174 No. 3/4, 87–94). This article recalls that no vaccine against canine herpesvirosis is currently marketed and suggests that it would be useful to be able to vaccinate latent infected breeders in order to attenuate the re-excretion of the wild-type virus.

On the other hand, in her article (Rec. Med. Vet., 1982, 158, 669–676), F. Delisle proposes vaccinating bitches before gestation with an inactivated vaccine or injecting the puppies with a serum at whelping. She recalls, however, that no commercial vaccine is available. See also L. E. Carmichael, J. Am. Vet. Med. Assoc., 1970, 156, 1714–1721. In his article ("Canine Herpesvirus" in Virus Infections of Vertebrates, vol. 1, M. C. Horzinek, Ed. M. J. Appel, Elsevier Science Publisher, 1987, 5–15), A. Appel proposes vaccinating bitches before or at the very start of gestation with an inactivated vaccine.

H. Poulet and P. Dubourget (Point Vét., 1993, 25, 69–75) suggested in 1992, in general terms, the vaccination of the mother with a booster vaccination at the end of gestation. The authors also recall that tests using attenuated variants were carried out (L. E. Carmichael et al., Infection and Immunity, 1978, 20(1), 108–114; U.S. Pat. No. 4,213,965; attenuated live vaccine, composed of a heat-sensitive variant of the CHV virus, referred to as being "of small plaque"), but these tests did not yield any convincing results and did not lead to the marketing of vaccines.

In his article (Vet. Med., April 1991, 4, 394–403), J. O. Anvik points out that the production of neutralizing antibodies in the mother and consequently the protection of the litter is unpredictable on account of the low immunogenicity of the CHV virus.

Faced with the difficulty of vaccination, Pierson et al. (recueil de Médecine Vétérinaire, March/April 1998, 174 No.3/4, 87–94) even went as far as to propose vaccinating the mother with an inactivated vaccine against felid herpesvirus (FHV) or administering anti-FHV antibodies to puppies at whelping.

To date, none of the vaccination hypotheses has been confirmed, no vaccine is commercially available and no publication has presented convincing vaccination results announcing the impending marketing of such a vaccine.

In addition, in gestating bitches, infection with CHV can lead to embyronic resorption, fetal mummification, abortion or premature whelping, still-birth or neonatal mortality. Placental lesions may appear.

Although vaccines against various herpesviruses exist in other animal species, including cats, it has never been possible to propose effective vaccination against canine herpesvirosis.

The object of the present invention is to develop a method for vaccination against canine herpesvirosis which allows puppies to be protected.

Another object of the invention is to produce efficient and pharmaceutically acceptable vaccines which can be used in the context of this vaccination method.

The Applicant has found, surprisingly, that it is possible to vaccinate gestating bitches and newborn puppies by administering a vaccine during the gestation period and in particular as close as possible to whelping, so as to have a high level of anti-CHV antibodies in the gestating bitch at the time of whelping, this level providing protection to the puppies at whelping by transmission of the maternal antibodies during suckling. In addition, these antibodies are substantially maintained in the puppies during the first weeks of their life, this being the period during which they are prone to disease (3 to 4 weeks). A titer of neutralizing antibodies in the bitch of greater than or equal to 0.9 log10 is preferred, more particularly a titer greater than or equal to 1.2 log10. The titers indicated are calculated according to the method described in Example 7. Vaccination of the bitch moreover leads to a reduction in the pressure of infection in the puppies. The Applicant has moreover observed, in bitches vaccinated and maintained in a contaminated environment, a higher weight of puppies at whelping and a tendency toward a higher level of gestation. These phenomena can be explained by a reduction or absence of placental lesions in the vaccinated bitches (A. Hashimoto et al., Am. J. Vet. Res., 1979, 40(9), 1236–1240; A. Hashimoto et al., Am. J. Vet. Res., 1982, 43(5), 844–850).

The objects of the invention already mentioned, as well as others, are obtained with the aid of a method for immunizing or vaccinating gestating bitches which comprises the administration of an immunogenic composition or vaccine to a gestating bitch as close as possible to whelping, in particular during the final third of gestation (the average duration of gestation in dogs is about 63 days), notably 1 to 20 days, in particular 1 to 15 days, more particularly 5 to 15 days, preferably 5 to 10 days before the presumed date of whelping, typically about 10 days before, so as to have a high level of anti-CHV antibodies in the gestating bitch at whelping, which induces protection of the puppies by transfer of the maternal antibodies during suckling. These antibodies are substantially maintained during the first weeks of life of the puppies, this being the period during which they are prone to disease (3 to 4 weeks).

By definition, an antigen, in an effective amount in the composition or vaccine according to the invention, makes it possible to induce a high and protective level of antibodies under the conditions of the protocol in the gestating bitch and the newborn puppy. This may be an antigen comprising the inactivated CHV virus, the attenuated CHV virus, one or more subunits of the CHV virus or one or more antigens expressed by recombinants.

Preferably, the immunogenic composition or the vaccine is intended to produce in the gestating bitch, at the time of whelping, a level of anti-CHV antibodies (determined according to example 7) of greater than or equal to about 0.9 log10, preferably greater than or equal to about 1.2 log10.

Especially in the case of an animal which has never been vaccinated against CHV, another (or several other) administration(s) of anti-CHV vaccine is preferably carried out before the administration described above in order to induce the immune response in the animal. The interval between these two administrations must be sufficient to induce a booster effect, which generally requires at least 2 to 3 weeks. The first administration of vaccine is notably done within a period which goes from oestrus and at least 2 or 3 weeks before the above described administration, in particular within the period which goes from oestrus to the first third of the gestation, including the first third of gestation, which period includes administration before insemination. Preferably this administration is done about 7 to 10 days before the insemination. According to a preferred embodiment, this vaccination scheme is applied for each whelping occurrence.

If the animal has already been vaccinated against CHV, a single administration close to whelping may suffice.

The administration, or at least one of the additional administrations, can also be carried out with a vaccine whose composition is different from that used as close as possible to whelping, the difference possibly lying in the antigen and/or the formulation of the vaccine.

The composition and vaccine can be administered especially via the parenteral route, preferably via the subcutaneous or intramuscular route.

The dose volumes can be, in particular, between 0.2 and 2 ml, preferably about 1 ml.

A subject of the invention is also the use of CHV antigen to prepare an immunogenic composition or a vaccine against canine herpesvirosis, which is intended to be administered according to the protocol described above.

A person skilled in the art has the competence required to accurately define the doses of each composition or vaccine as a function of the type of composition or vaccine.

When several administrations are performed on the animal, the compositions or vaccines used can be of different types, chosen in particular from those mentioned above.

A subject of the invention is also inactivated immunogenic compositions and vaccines or subunit immunogenic compositions and vaccines, which can be used in particular in the context of this method of vaccination.

The use of CHV subunits has only been described in mice (J. A. Limcumpao et al., J. Vet. Med. Sci., 1991, 53(3), 423–432). However, the data obtained in mice cannot be extrapolated to the canine species, as stated in that document. Although the antibody titers obtained with the purified glycoproteins gp145/112, gp80 and gp47 induce a detectable antibody response, it is not possible, however, to determine whether or not this antibody titer may he reflected by a protection since, as mice are not sensitive to the CHV virus, it is not possible to develop a virulent challenge model in this species. Furthermore, no data are available regarding the cellular immunity induced by CHV. Moreover, the relationship between the antibody titer obtained in mice and that obtained in dogs is unknown and these titers may prove to be different. Thus, it has been published that rabbits immunized with type 1 bovine herpes glycoprotein gI have a higher neutralizing titer than rabbits immunized with gIII, whereas in cattle, the glycoprotein gIV induces the highest neutralizing titer and the glycoprotein gI is the least immunogenic. These data show the difficulty of transposing results from laboratory animals to the target species.

In accordance with the invention, the use of an inactivated immunogenic composition and vaccine or of subunits allows the immunization or vaccination of bitches during the gestation phase without any risk to the bitch or its offspring. Vaccination with booster at the end of gestation is the means for assuring an optimum titer of neutralizing antibodies at whelping. This titer conditions the protection obtained by transfer of neutralizing antibodies from the bitch to its puppies at the start of suckling.

The CHV virus is preferably cultured and propagated on primary canine cells or on a cell line, more particularly on canine kidney cells of a line such as MDCK (Madin-Darby Canine Kidney, available from the American Type Culture Collection (ATCC) under the number CCL-34) in particular with a multiplicity of infection (moi) of from 0.1 to 0.001 tissue culture infective doses 50% ($TCID_{50}$) per cell, preferably 0.01 $TCID_{50}$/cell. The CHV virus is harvested 3 to 4 days later. A viral titer of about $10^6$ to $10^8$ $TCID_{50}$/ml and in general from $10^{6.5}$ to $10^{7.5}$ $TCID_{50}$/ml may be obtained.

In order to obtain an inactivated immunogenic composition or vaccine, the CHV virus is preferably inactivated after harvesting and clarification by means of a chemical treatment (e.g. formalin or formaldehyde, β-propiolactone, ethyleneimine, binary ethyleneimine (BEI)) and/or a heat treatment. Preferably, the virus according to the invention is inactivated by the action of ethyleneimine. The viral particles can be concentrated by conventional concentration techniques, in particular by ultrafiltration and/or purified by conventional purification means, in particular techniques of gel-filtration, ultracentrifugation on a sucrose gradient or selective precipitations, in particular in the presence of polyethylene glycol (PEG).

The subunit immunogenic composition or vaccine is preferably an extraction subunit one, namely is prepared from the whole virus or from a main fraction of this virus (for instance after elimination of capsid). In particular, this immunogenic composition or vaccine may comprise the various envelope glycoproteins or a mixture of envelope glycoproteins. The subunit immunogenic compositions and vaccines are preferably produced from an inactivated viral suspension, in particular inactivated as described above. Preferably, in order to obtain a subunit immunogenic composition or vaccine, mainly containing the envelope glycoproteins, the suspension of viral particles, preferably inactivated, obtained above, is subjected to the action of a suitable detergent, in particular a nonionic detergent, preferably an ethoxylated alcohol advantageously with an HLB of between 12 and 15. The viral capsids are then removed, in particular by ultracentrifugation. Other equivalent methods for removing the capsids and collecting the envelope glycoproteins are available to those skilled in the art.

In order to develop an inactivated immunogenic composition or vaccine or a subunit immunogenic composition or vaccine, the antigen is taken up in a veterinarilly acceptable vehicle or excipient and a veterinarilly acceptable adjuvant is preferably added thereto. The amount of antigen is equivalent in particular to a titer before inactivation of about $10^5$ to about $10^{9.5}$ TCID$_{50}$, particularly from about $10^5$ to about $10^9$ TCID$_{50}$, per dose. More particularly, for an inactivated composition or vaccine, the titer before inactivation is of about $10^5$ to about $10^9$ TCID$_{50}$, particularly from about $10^6$ to about $10^8$ TCID$_{50}$, per dose. More particularly for a subunit composition or vaccine, the titer before inactivation is of about $10^6$ to about $10^{9.5}$, particularly from about $10^7$ to about $10^9$, preferably from about $10^{7.5}$ to about $10^{8.5}$, per dose. Preferably, for a subunit vaccine, the vaccine has a glycoprotein gB titre as measured in ELISA of about 0.01 μg to about 30 μg, in particular from about 0.1 μg to about 10 μg, preferably from about 0.3 μg to about 3 μg per dose.

The immunogenic compositions and vaccines according to the invention are conserved and stored either in formulated form at 5° C., or in lyophilized form, preferably with a stabilizer, in particular SPGA (sucrose, phosphate, glutamate, albumin, EP-B1-0 008 255). These immunogenic compositions and vaccines may be taken up subsequently in solvent (vehicle or excipient and/or adjuvant).

In order to adjuvate the immunogenic compositions and vaccines according to the invention, it is possible to use (1) aluminum hydroxide, (2) an acrylic acid or methacrylic acid polymer, a polymer of maleic anhydride and of alkenyl derivative, (3) an immunostimulating sequence (ISS), in particular an oligodeoxyribonucleotidic sequence bearing one or more non-methylated CpG groups (Klinman D. M. et al., Proc. Natl. Acad. Sci. USA, 1996, 93, 2879–2883 ; WO-A-9816247), or (4) to formulate the immunogenic or vaccine preparation in the form of an oil-in-water emulsion, in particular the SPT emulsion described on page 147 of "Vaccine Design, The Subunit and Adjuvant Approach" edited by M. Powell and M. Newman, Plenum Press, 1995, and the emulsion MF59 described on page 183 of this same book.

The oil-in-water emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycerol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic®, block copoymers of propyleneoxide and ethylene, oxide products, especially L121.

The acrylic acid or methacrylic acid polymers are crosslinked in particular with polyalkenyl ethers of sugars or of polyalcohols. These compounds are known under the term "carbomer" (Pharmeuropa vol. 8, No. 2, June 1996). A person skilled in the art may also refer to U.S. Pat. No. 2,909,462 (incorporated by reference) describing such acrylic polymers crosslinked with a polyhydroxylated compound containing at least 3 hydroxyl groups, preferably not more than 8, the hydrogen atoms of at least 3 hydroxyls being replaced with unsaturated aliphatic radicals containing at least 2 carbon atoms. The preferred radicals are those containing from 2 to 4 carbon atoms, e.g. vinyls, allyls and other ethylenically unsaturated groups. The unsaturated radicals can themselves contain other substituents, such as methyl. The products sold under the name Carbopol®, polymers of acrylic acid crosslinked with allylsucrose or allylpentaerythritol, (BF Goodrich, Ohio, USA) are particularly suitable. They are crosslinked with an allyl sucrose or with allylpentaerythritol. Among these, mention may be made of the products Carbopol® 974P, 934P and 971P.

Among the copolymers of maleic anhydride and of an alkenyl derivative, those which are preferred are the EMA® products, copolymers of maleic annhydride and of ethylene, (Monsanto) which are copolymers of maleic anhydride and of ethylene, which may be linear or crosslinked, for example crosslinked with divinyl ether. Reference may be made to J. Fields et al., Nature, 186, 778–780, Jun. 4, 1960 (incorporated by reference). As regards their structure, the acrylic acid or methacrylic acid polymers and the EMA® products are preferably formed from units based on the following formula:

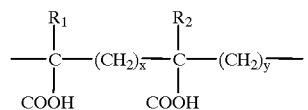

in which:
R$_1$ and R$_2$, which may be identical or different, represent H or CH$_3$
x=0 or 1, preferably x=1
y=1 or 2, with x+y=2.
For the EMA® products, x=0 and y=2. For the carbomers, x=y=1.

The polymer concentration in the final vaccine composition will be from 0.01% to 1.5% W/V, more particularly from 0.05 to 1% W/V, preferably from 0.1 to 0.4% W/V.

One form of immunogenic composition or vaccine which is particularly preferred comprises an inactivated immunogenic composition or vaccine or a subunit immunogenic composition or vaccine formulated in the form of an oil-in-water emulsion comprising anhydromannitol oleate, ethoxylated oleic acid and light liquid paraffin oil. In particular, a method for immunizing gestating bitches according to the invention comprises the administration of such an immunogenic composition or vaccine. Two injections are given, preferably subcutaneously, in particular in accordance with the above-described scheme, for example with the first injection during the first third of the gestation, preferably about 10 days after the date of insemination and in particular the second injection during the final third, preferably about 10 days before the presumed date of whelping.

A subject of the invention is also the process for preparing the inactivated immunogenic compositions and vaccines or the subunit immunogenic compositions and vaccines described.

A subject of the invention is also multivalent immunogenic compositions and vaccines comprising the inactivated canine herpesvirus valency or the canine herpesvirus subunit valency, and at least one valency for at least one other canine pathogen, in a veterinarially acceptable vehicle or excipient and preferably with an adjuvant, especially one of those described above.

Said canine pathogens are chosen in particular from the group comprising canine distemper virus, canine parvovirus and canine adenovirus, but other valencies may also be combined.

The inactivated CHV immunogenic compositions and vaccines or subunit immunogenic compositions and vaccines according to the invention can be administered simultaneously in the same preparation or successively in different preparations with the other canine valency (valencies) which may be in the form of attenuated live, inactivated, subunit, recombinant, or polynucleotide immunogenic compositions and vaccines.

A subject of the invention is thus also a multivalent vaccine kit or pack comprising, separately packaged, a CHV valency according to the invention in a veterinarially acceptable vehicle or excipient, and preferably with an adjuvant, in particular those described above, and at least one valency of at least one other canine pathogen. The CHV valency according to the invention can serve as a solvent for the other canine valency, in particular for an attenuated, recombinant or polynucleotide valency in lyophilized form.

The invention will now be described in greater detail with the aid of embodiments given as non-limiting examples.

EXAMPLES

Example 1

Viral Strain

The strain of canine herpesvirus used is the strain F205 (L. E. Carmichael, Am. J. Vet. Res., 1965, 26, 803–814), available from the American Type Culture Collection (ATCC) under the number VR-647.

Example 2

Amplification of the Canine Herpesvirus

Cells of a canine line (Madin-Darby Canine Kidney or MDCK, available from the ATCC under the number CCL-34) are cultured in 2-liter rolling flasks (850 cm$^2$) with Dulbecco modified Eagle's minimum essential medium (DMEM-Gibco BRL) supplemented with 5% fetal calf serum (Bayer Diagnostic) and gentamycin at a concentration of 50 mg/l in a proportion of 200,000 cells per ml under a volume of 350 ml. The cells are cultured at +37° C. in an atmosphere containing 5% $CO_2$.

After 3 or 4 days, the cell layer reaches confluence. The culture medium is then replaced with serum-free DMEM medium still supplemented with 50 mg/l of gentamycin, and the cells are inoculated with canine herpesvirus (Example 1) with a multiplicity of infection (moi) of 0.01 $TCID_{50}$/cell. The viral culture is maintained at 37° C.

When the cytopathic effect (CPE) is complete (about 96 hours after the start of culturing), the viral suspension is harvested and frozen at −70° C. Several cell amplification passages can be carried out prior to the viral inoculation depending on the amount of virus desired. The cell passages and the viral culturing can also be carried out by culturing the cells on microcarriers in a biogenerator.

The virus is conserved at 5° C. until the following steps.

The titer of the CHV virus at harvest is $10^{7.2}$ $TCID_{50}$ per ml.

Example 3

Titration of the CHV Virus

Titration of the CHV virus is carried out in 96-well microplates in F15 medium supplemented with 5% fetal calf serum and 50 mg/l of gentamycin. Dilutions with a rate of about 3 of the viral suspension are mixed with a suspension of MDCK cells in the microplate in a proportion of 0.10 ml of virus dilution per 100,000 cells in 0.15 ml per well. After incubation for 4 to 5 days at 37° C. with 5% $CO_2$, the wells with a generalized CPE are counted and the titer is calculated as tissue culture infectious doses (50%) ($TCID_{50}$) by the Kärber method.

Example 4

Inactivation of the Virus

The CHV virus amplified as described in Example 2 is inactivated with ethyleneimine at a concentration of about 12 mM, at 37° C. for 6 hours.

The ethyleneimine is prepared at the time of use by dissolving 28.0 g of sodium hydroxide pellets in 200 ml of distilled water and adding 68.1 g of bromoethylamine (BEA) corresponding to a 1.2 M solution of ethyleneimine (H. Bahnemann, Arch. Virol., 1975, 47, 47–56). The inactivated viral suspension is concentrated 100-fold on an ultrafiltration cassette of the Ultrasette type with a cutoff threshold of 300 kDa (Filtron). The concentrated inactivated virus can be frozen and stored at −40° C.

Example 5

Extraction of the Viral Glycoproteins

The inactivated virus (Example 4) is clarified by centrifugation at 2500×g for 30 min. The supernatant liquid is then concentrated 50-fold on an ultrafiltration cassette of the Ultrasette type with a cutoff threshold of 300 kDa (Filtron). The concentrate is supplemented with polyethylene glycol 8000 (PEG 8000) at a concentration of 8% W/V and 4% W/V sodium chloride. After contact for 16 hours at 4° C., the precipitated virus is sedimented by centrifugation at 2500×g for 60 min and then taken up in phosphate buffer (PBS: 8 g/l NaCl; 0.2 g/l KCl; 0.2 g/l $KH_2PO_4$; 1.44 g/l $Na_2HPO_4.2H_2O$). It is then taken up in isotonic phosphate buffer in a proportion of one hundredth of the initial volume. The viral concentrate then undergoes a zonal ultracentrifugation on a cushion of sucrose (35% and 60% W/W PBS, for 60 min at 200,000×g) with a zonal rotor or a Ti45 fixed-angle rotor. The virus is harvested at the interface and is diluted approximately four-fold with PBS. Next, 10 EO cetyl alcohol (ethoxylated alcohol of HLB 13) at a concentration of 1.5% W/V is added, and the mixture is incubated for one hour at 37° C. The capsids are then sedimented by ultracentrifugation for one hour at 230,000×g with a Ti45 rotor. The supernatant containing the glycoproteins is collected. The glycoprotein solution can optionally be concentrated by ultrafiltration.

The solution of purified glycoproteins is stored at −40° C. until formulation of the vaccine.

Example 6
Formulation of the Vaccines

The concentrated inactivated antigen (Example 4) or the solution of subunits (Example 5), after thawing, is diluted in PBS buffer as a function of the required amount of antigens per dose.

The adjuvant-containing vaccine is prepared in the following way: 167 ml of aqueous phase consisting of 8 ml of subunit or inactivated viral antigen and 159 ml of PBS are emulsified in 83 ml of oily phase containing 7% w/v of anhydromannitol oleate, 8% w/v of oleic acid ethoxylated with 11 EO (ethylene oxide) and 85% v/v of light liquid paraffin oil (European Pharmacopea type) with the aid of a Silverson emulsifying turbomixer at 32° C. for 2 minutes. The vaccine formulated in the form of an oil-in-water emulsion is then stored at 5° C.

An alternative method for preparing the vaccine consists in emulsifying, by three passages through a model Y110 high-pressure homogenizer (Microfluidics Corp.) at a pressure of 600 bar and at a temperature of between 30 and 40° C., a mixture of 5% w/v squalane, 2.5% w/v Pluronic® L121, 0.2% w/v of an ester of oleic acid and of anhydrosorbitol ethoxylated with 20 EO, 92.3% v/v of the viral antigen diluted 30-fold in PBS buffer after thawing. The vaccine formulated in the form of an oil-in-water emulsion is then stored at 5° C.

Another alternative method consists in preparing a solution containing 0.4% w/v of Carbopol® 974P in physiological saline (9 g/l NaCl). The pH is adjusted to 7.3–7.4 with sodium hydroxide. This Carbopol solution is then mixed in equal parts with the viral antigen diluted 16-fold after thawing. The vaccine formulated in the form of a suspension is then stored at 5° C.

0.5 ml of a solution of subunits (Example 5), after thawing, diluted 15-fold in PBS buffer, is added to 0.5 ml of SPGA lyophilization substrate (sucrose, phosphate, glutamate, albumin, EP-B1-0 008 255). This mixture is divided among flasks and lyophilized and then stored at 5° C. The diluent consists of the adjuvants described above incorporating only PBS buffer in the aqueous phase.

Example 7
Titration of the Anti-CHV Neutralizing Antibodies

The sera to be titrated are tested for their ability to neutralize the CHV virus. The sera taken from the animals are diluted in cascade three-fold with DMEM medium supplemented with 5% fetal calf serum in 96-well cell culture plates. 0.05 ml of culture medium containing approximately 200 $TCID_{50}$/ml of CHV is added to 0.05 ml of diluted serum. This mixture is incubated for 2 hours at 37° C. in an oven under an atmosphere containing 5% $CO_2$.

0.15 ml of an MDCK cell suspension containing about 100,000 cells per ml is then added to each mixture. The cytopathic effect (CPE) is observed by phase-contrast microscopy after culturing for 5 days at 37° C. under an atmosphere containing 5% $CO_2$. The neutralizing titers of each serum are calculated according to the Kärber method. The titers are given in the form of the highest dilution which inhibits the cytopathic effect for 50% of the wells. The titers are expressed as log10 VN50. Each serum is titrated at least twice and preferably four times.

Example 8

Efficacy 12 non-vaccinated EOPS Beagle bitches were included in the study and divided randomly into 2 groups of six animals. The bitches of the first group are vaccinated with the CHV subunit vaccine adjuvanted with the oil-in-water emulsion based on paraffin oil (Example 6), and the bitches of the other group are vaccinated with a placebo vaccine.

The bitches were vaccinated twice subcutaneously about 10 days after insemination, and then about 10 days before the presumed date of whelping. The lyophilizate taken up in 1 ml of oily solvent is administered to the bitches. It corresponds to a titer equivalent of $10^{7.7}$ $TCID_{50}$ before inactivation.

After whelping, the newborn puppies are tested at the 3-day-old stage with 50 to 100 $TCID_{50}$ of a virulent strain of CHV, for example F205 isolated by L. E. Carmichael (Am. J. Vet. Res., 1965, 26, 803–814) or CHV 270 (H. Hill, Am. J. Vet. Res., 1974, 35, 669–673) or CHV C4012SE, via the oronasal route (0.5 ml orally and 0.25 ml in each nostril). The puppies are then observed for 3 weeks. The clinical signs and mortality are recorded. After their death, all the puppies are autopsied. The macroscopic lesions characteristic of canine herpesvirosis are searched for in the kidneys, spleen, liver, lungs, digestive tract, heart and mesenteric ganglia, and samples are taken for isolation of CHV on MDCK cells. The diagnosis of canine herpesvirosis is based on the death of the puppy and the presence of characteristic macroscopic lesions and is confirmed by a viral isolation.

All the vaccinated bitches underwent seroconversion and had a high titer of neutralizing antibodies at the time of whelping. These titers are measured by the method described in Example 6 and are expressed as log10 VN50.

| Average anti-CHV SN titers in the bitches | Day of the first vaccination | Day of the booster vaccination | Day of the test | 3 weeks after test |
|---|---|---|---|---|
| Control group | <0.24 ± 0.00 | <0.24 ± 0.00 | <0.29 ± 0.13 | <1.36 ± 0.65 |
| vaccinated group | <0.35 ± 0.17 | <1.04 ± 0.34 | 1.76 ± 0.20 | 2.11 ± 0.51 |

Among the puppies born from vaccinated mothers, none of them died from canine herpesvirosis (0/27). No CHV virus was re-isolated from these puppies.

Among the puppies born from non-vaccinated mothers (placebo group), a mortality rate due to CHV of 62% (18/29) was observed. Viral isolation is also observed in 55% of these puppies (16/29): samples from two puppies were contaminated with bacteria and could not be tested for the viral isolation of CHV.

The difference in the mortality rate between the 2 groups is highly significant (Fisher exact test; $p<0.0001$).

Yorkshire terrier bitches divided randomly into 2 groups are kept in an infected environment. The 14 bitches of the first group are vaccinated with the CHV subunit vaccine adjuvated with an oil-in-water emulsion based on paraffin oil (Example 6) and the 6 bitches of the other group are vaccinated with a placebo vaccine. The vaccination protocol is identical to that described above.

The weight of the puppies is measured at whelping.

The weight of the 28 puppies born from a vaccinated mother is substantially higher (average weight of 141.8 g) than that of the 14 puppies born from a non-vaccinated mother (average weight of 85.0 g), i.e. a weight gain of 166.8%. The difference is significant (Kruskal-Wall is, $p<0.01$).

The results show, in a contaminated environment, a tendency to increase the level of gestation in the vaccinated bitches.

The level of gestation is 82% in the vaccinated bitches (50/61) and 68% in the non-vaccinated bitches (placebo group) (19/28) (Fisher exact test, p=0.11).

It should be clearly understood that the invention defined by the attached claims is not limited to the specific embodiments indicated in the description above, but encompasses the variants which do not emerge either from the scope or spirit of the present invention.

What is claimed is:

1. A method for protecting a puppy against Canine HerpesVirus (CHV) comprising administering to the mother of the puppy, 1 to 20 days prior to whelping, a vaccine comprising: inactivated CHV or glycoprotein-extract from inactivated CHV, and an adjuvant.

2. The method according to claim 1, wherein the adjuvant is aluminum hydroxide.

3. The method according to claim 1, wherein the adjuvant is an acrylic acid or methacrylic acid polymer or a polymer of maleic anhydride and alkenyl derivative.

4. The method according to claim 3, wherein the adjuvant is polymers of acrylic acid crosslinked with allyl sucrose or allylpentaerythritol.

5. The method according to claim 1, wherein the adjuvant is an immunostimulating sequence.

6. The method according to claim 1, wherein the vaccine is formulated in the form of an oil-in-water emulsion.

7. The method according to claim 6, wherein the oil-in-water emulsion comprises either anhydromannitol oleate, ethoxylated oleic acid and light liquid paraffin oil, or block copolymers of propyleneoxide and ethylene oxide, ester of sorbitan and of ethoxylated oleic acid and squalane.

8. The method according to claim 1, wherein the vaccine is obtained from a CHV virus inactivated by a chemical and/or heat treatment.

9. The method according to claim 1, wherein the vaccine is obtained from reacting a CHV culture with a detergent.

10. The method according to claim 9, wherein the detergent is a nonionic detergent.

11. The method according to claim 10, wherein the detergent is an ethoxylated alcohol with an HLB of between 12 and 15.

12. The method according to claim 11, wherein the detergent is 10 EO cetyl alcohol.

13. The method according to claim 1, wherein the vaccine comprises a glycoprotein gB titre as measured in ELISA of about 0.01 $\mu$g to about 30 $\mu$g.

14. The method according to claim 1, wherein the vaccine contains a mixture of CHV proteins which comprise envelope glycoproteins.

15. The method according to claim 14, wherein the mixture of CHV proteins does not comprise the capsid protein.

16. The method of claim 1, wherein the vaccine is prepared by a process comprising the steps of:
   (a) contacting CHV with a detergent to form a suspension,
   (b) removing CHV capsids from the suspension to thereby form a remaining suspension, and
   (c) collecting the remaining suspension.

17. The method according to claim 16, wherein the detergent is a nonionic detergent.

18. The method according to claim 16, wherein the detergent is an ethoxylated alcohol with an HLB of between 12 and 15.

19. The method according to claim 16, wherein the detergent is 10 EO cetyl alcohol.

20. The method according to claim 16, wherein the CHV is inactivated prior to contacting with the detergent.

21. The method according to claim 17, wherein the CHV is inactivated with a chemical agent selected from the group consisting of formalin, $\beta$-propiolactone, ethyleneimine and binary ethyleneimine.

22. The method according to claim 18, wherein the CHV is inactivated by ethyleneimine.

23. The method according to any one of claims 10–15, or 16–22, wherein the adjuvant aluminum hydroxide.

24. The method according to any one of claims 10–15, or 16–22, wherein the adjuvant is an acrylic acid or methacrylic acid polymer or a polymer of maleic anhydride and alkenyl derivative.

25. The method according to any one of claims 10–15, 16–22, wherein the vaccine is formulated as an oil-in-water emulsion.

26. The method of claim 1, wherein the vaccine comprises a mixture of CHV proteins obtained after contacting a CHV culture with a detergent, wherein the vaccine is formulated as an oil-in-water emulsion.

27. The method according to claim 26, wherein the oil-in-water emulsion comprises anhydromannitol oleate, ethoxylated oleic acid and light paraffin oil.

28. The method according to claim 26, wherein the oil-in-water emulsion comprises block copolymers of propyleneoxide and ethylene oxide, ester of sorbitan and ethoxylated oleic acid and squalane.

29. The method according to claim 26, wherein the detergent is a nonionic detergent.

30. The method according to claim 26, wherein the detergent is an ethoxylated alcohol with an HLB of between 12 and 15.

31. The method according to claim 26, wherein the detergent is 10 EO cetyl alcohol.

32. The method according to claim 26, wherein the mixture of CHV proteins comprises envelope glycoproteins.

33. The method according to claim 26, wherein the mixture of CHV proteins does not comprise the capsid protein.

34. The method of claim 1, wherein the vaccine is prepared by a process comprising the steps of:
   (a) contacting CHV with a detergent to form a suspension,
   (b) removing the CHV capsids from the suspension to thereby form a remaining suspension,
   (c) collecting the remaining suspension as a mixture of proteins in an oil-in-water emulsion.

35. The method according to claim 34, wherein the oil-in-water emulsion comprises anhydromannitol oleate, ethoxylated oleic acid and light paraffin oil.

36. The method according to claim 34, wherein the oil-in-water emulsion comprises block copolymers of propyleneoxide and ethylene oxide, ester of sorbitan and ethoxylated oleic acid and squalane.

37. The method according to claim 34, wherein the detergent is a nonionic detergent.

38. The method according to claim 34, wherein the detergent is an ethoxylated alcohol with an HLB of between 12 and 15.

39. The method according to claim 34, wherein the detergent is 10 EO cetyl alcohol.

40. The method according to claim 34, wherein the CHV is inactivated prior to contacting with the detergent.

41. The method according to claim 40, wherein the CHV is inactivated with a chemical agent selected from the group consisting of formalin, $\beta$-propiolactone, ethyleneimine and binary ethyleneimine.

42. The method according to claim 41, wherein the CHV is inactivated by ethyleneimine.

43. The method according to any one of claims 14, 15, 16, 26 or 34, comprising a glycoprotein gB titre, as measured in ELISA of about 0.01 μg to about 30 μg per dose.

44. The method of claim 1, wherein the administering to the mother is by subcutaneous delivery.

45. The method of claim 1, wherein the administering to the mother is during 1–15 days prior to whelping.

46. The method of claim 1, wherein the administering to the mother is during 5–15 days prior to whelping.

47. The method of claim 1, wherein the administering to the mother is about 10 days prior to whelping.

48. The method of claim 1, wherein the administering to the mother 1–20 days prior to whelping is a latter administration of at least two administrations of the vaccine which are separated in time such that there is a booster effect.

49. The method of claim 48, wherein the administrations are separated in time by 2–3 weeks.

50. The method of claim 48, wherein an administration of the vaccine occurs after oestrus which results in the whelping.

51. The method of claim 50, wherein the administration of the vaccine after the oestrus which results in the whelping occurs before insemination.

52. The method of claim 51, wherein the administration of the vaccine after the oestrus which results in the whelping occurs 7–10 days before insemination.

53. The method of claim 50, wherein the administration of the vaccine after the oestrus which results in the whelping occurs after insemination.

54. The method of claim 53, wherein the administration of the vaccine after the oestrus which results in the whelping is about 10 days after insemination.

55. The method of claim 54, wherein there are two administrations of the vaccine at about 10 days after insemination.

56. The method of claim 55, wherein the administering to the mother 1–20 prior to whelping is at about 10 days prior to whelping.

57. The method of claim 56, wherein the administrations are subcutaneous.

58. The method of claim 48, wherein the administrations are subcutaneous.

59. The method of any one of claims 1 or 47–58, wherein the mother suckles the puppy.

* * * * *

UNITED STATES PATENT AND TRADEMARK OFFICE
CERTIFICATE OF CORRECTION

PATENT NO.    : 6,551,598 B2
DATED         : April 22, 2003
INVENTOR(S)   : Herve Poulet It is certified that error appears in the above-identified patent and that said Letters Patent is hereby corrected as shown below:

<u>Title page,</u>
Item [73], Assignee, change "Lyons" to -- Lyon --

<u>Column 12,</u>
Line 10, change "the adjuvant aluminum hydroxide" to -- the adjuvant is aluminum hydroxide --.

Signed and Sealed this

Twenty-first Day of October, 2003

JAMES E. ROGAN
*Director of the United States Patent and Trademark Office*